(12) United States Patent
Flanagan

(10) Patent No.: US 11,604,143 B2
(45) Date of Patent: Mar. 14, 2023

(54) SPATIAL GRADIENT-BASED FLUOROMETER

(71) Applicant: YSI, INC., Yellow Springs, OH (US)

(72) Inventor: Kevin Flanagan, Yellow Springs, OH (US)

(73) Assignee: YSI, INC., Yellow Springs, OH (US)

( * ) Notice: Subject to any disclaimer, the term of this patent is extended or adjusted under 35 U.S.C. 154(b) by 0 days.

(21) Appl. No.: 17/324,475

(22) Filed: May 19, 2021

(65) Prior Publication Data

US 2021/0364438 A1  Nov. 25, 2021

Related U.S. Application Data

(60) Provisional application No. 63/027,587, filed on May 20, 2020, provisional application No. 63/028,013, (Continued)

(51) Int. Cl.
*G01N 21/64* (2006.01)
*G01N 33/18* (2006.01)
(Continued)

(52) U.S. Cl.
CPC ..... *G01N 21/6456* (2013.01); *G01N 21/4785* (2013.01); *G01N 21/532* (2013.01); *G01N 21/64* (2013.01); *G01N 21/82* (2013.01); *G01N 33/18* (2013.01); *H04N 5/347* (2013.01); *G01N 2021/6473* (2013.01); (Continued)

(58) Field of Classification Search
CPC ....... G01N 21/6456; G01N 2201/0633; G01N 2201/12792; H04N 5/347
See application file for complete search history.

(56) References Cited

U.S. PATENT DOCUMENTS

| 5,257,202 A | 10/1993 | Feddersen et al. |
| 5,436,476 A * | 7/1995 | Hynecek ................ G11C 27/04 257/224 |

(Continued)

FOREIGN PATENT DOCUMENTS

WO    2015/089631 A1    6/2015

OTHER PUBLICATIONS

Moe, Andrew E., et al. "Improvements in LED-based fluorescence analysis systems." Sensors and Actuators B: Chemical 111 (2005): 230-241. http://labs.ece.uw.edu/denise/www/Lab/publications/journal/j2005_0 1.pdf; pp. 230-241.

(Continued)

*Primary Examiner* — Marcus H Taningco
(74) *Attorney, Agent, or Firm* — Ware, Fressola, Maguire & Barber LLP

(57) ABSTRACT

A spatial gradient-based fluorometer featuring a signal processor or processing module configured to: receive signaling containing information about light reflected off fluorophores in a liquid and sensed by a linear sensor array having a length and rows and columns of optical elements; and determine corresponding signaling containing information about a fluorophore concentration of the liquid a fluorophore concentration of the liquid that depends on a spatial gradient of the light reflected and sensed along the length of the linear sensor array, based upon the signaling received.

20 Claims, 8 Drawing Sheets

Related U.S. Application Data filed on May 21, 2020, provisional application No. 63/028,723, filed on May 22, 2020.

(51) Int. Cl.
    *G01N 21/47*     (2006.01)
    *G01N 21/53*     (2006.01)
    *G01N 21/82*     (2006.01)
    *H04N 5/347*     (2011.01)

(52) U.S. Cl.
    CPC ........... *G01N 2021/6491* (2013.01); *G01N 2201/061* (2013.01); *G01N 2201/0633* (2013.01); *G01N 2201/0636* (2013.01); *G01N 2201/126* (2013.01); *G01N 2201/12761* (2013.01); *G01N 2201/12792* (2013.01)

(56) References Cited

U.S. PATENT DOCUMENTS

| | | | |
|---|---|---|---|
| 6,013,034 | A | 1/2000 | Fernandes Da Cunha Vaz et al. |
| 6,255,118 | B1 | 7/2001 | Alfano et al. |
| 6,303,316 | B1 | 10/2001 | Kiel et al. |
| 6,369,894 | B1 | 4/2002 | Rasimas et al. |
| 6,670,617 | B2 | 12/2003 | Banks |
| 6,825,927 | B2 | 11/2004 | Goldman et al. |
| 6,852,986 | B1 | 2/2005 | Lee et al. |
| 6,929,730 | B2 | 8/2005 | Lee et al. |
| 7,095,500 | B2 | 8/2006 | Banks |
| 7,968,856 | B2 | 6/2011 | Lee et al. |
| 8,721,858 | B2 | 5/2014 | Chambers et al. |
| 10,036,703 | B1 * | 7/2018 | Ng ................ G01N 21/255 |
| 2002/0017612 | A1 * | 2/2002 | Yu ................ H01L 51/4206 250/370.11 |
| 2003/0055233 | A1 | 3/2003 | Krull |
| 2004/0130716 | A1 * | 7/2004 | Couston ............ G01N 21/6456 356/318 |
| 2006/0109475 | A1 | 5/2006 | Misener et al. |
| 2007/0128658 | A1 | 6/2007 | Blackwell et al. |
| 2011/0207142 | A1 | 8/2011 | Lee et al. |
| 2012/0223260 | A1 | 9/2012 | Hansen et al. |
| 2014/0080122 | A1 | 3/2014 | Strano et al. |
| 2016/0178618 | A1 | 6/2016 | Freyer et al. |
| 2017/0038301 | A1 | 2/2017 | Flanagan et al. |
| 2018/0231465 | A1 | 8/2018 | Rothberg et al. |
| 2019/0033205 | A1 | 1/2019 | Egalon |
| 2019/0162662 | A1 | 5/2019 | Raphael et al. |

OTHER PUBLICATIONS

Trtilek, Martin, et al. "Dual-modulation LED kinetic fluorometer." Journal of luminescence 72 (1997); https://www.researchgate.net/profile/Michal_Koblizek/publication/257067891_Dualmodulation_LED_kinetic_fluorometer/links/5b8ce230299bf1d5a73a106e/Dualmodulation-LED-kinetic-fluorometer.pdf; pp. 597-599.

Chodavarapu, Vamsy P., et al. "CMOS-based phase fluorometric oxygen sensor system." IEEE Transactions on Circuits and Systems I: Regular Papers 54.1 (2007); http://www.eng.bu ffalo.edu/Departments/ee/faculty/cartwright/research/public ations_files/Journals/2007_IEEE_Trans_Circuits_Sys_I_v54_1_111.pdf; pp. 111-118.

Blockstein, Lior, and Orly Yadid-Pecht. "Lensless miniature portable fluorometer for measurement of chlorophyll and CDOM in water using fluorescence contact imaging." IEEE Photonics Journal 6.3 (2014); https://ieeexplore.ieee.org/iel7/4563994/6809260/0 6824241.pdf; pp. 1-16.

English Abstract of EP 3083983A1.

* cited by examiner

Linear Array Algorithm

$$-\ln(S(l)) = (\alpha[c])l + (-\ln([c]AT_0))$$

takes form of: $y = mx + b$

- Yields simple slope-intercept form (the slope contains the concentration)
- We do <u>not</u> need knowledge of the pesky intercept term, b $[c]$ = concentration
$\alpha$ = species absorption coefficient (system constant)
$l$ = length (location along the array)
$S(l)$ = sigal of array element at length, $l$

*FIG. 5*

Apparatus, including a spatial gradient-based fluorometer, 10

A quasi-collimated light source 20 configured to provide quasi-collimated light on a liquid having fluorophores.

A linear sensor array 30 having a length and row and columns of optical elements and configured to sense light reflected off the fluorophores in the liquid and provide signaling containing information about light reflected off the fluorophores.

A photodiode 30a configured at an end of the linear array

Signal processor or processing module 40 configured at least to: receive the signaling; and determine corresponding signaling containing information about a fluorophore concentration of the liquid that depends on a spatial gradient of the light reflected and sensed along the length of the linear sensor array, based upon the signaling received.

Other signal processor circuits, circuitry, or components 50 that do not form part of the underlying invention, e.g., including input/output modules/modems, one or more memory modules (e.g., RAM, ROM, etc.), data, address and control busing architecture, etc.

*FIG. 6*

| (r1, c1) | (r1, c2) | (r1, c3) | (r1, c4) | (r1, c5) | (r1, c6) | (r1, c7) | (r1, c8) | ··· | (r1, cn) |
|---|---|---|---|---|---|---|---|---|---|
| (r2, c1) | (r2, c2) | (r2, c3) | (r2, c4) | (r2, c5) | (r2, c6) | (r2, c7) | (r2, c8) | ··· | (r2, cn) |
| (r3, c1) | (r3, c2) | (r3, c3) | (r3, c4) | (r3, c5) | (r3, c6) | (r3, c7) | (r3, c8) | ··· | (r3, cn) |
| | | | | | ⋮ | | | | |
| (rn, c1) | (rn, c2) | (rn, c3) | (rn, c4) | (rn, c5) | (rn, c6) | (rn, c7) | (rn, c8) | ··· | (rn, cn) |

*FIG. 7*

SPATIAL GRADIENT-BASED FLUOROMETER

CROSS-REFERENCE TO RELATED APPLICATIONS

This application claims benefit to provisional patent application Ser. No. 63/027,587, filed 20 May 2020; 63/028,013, filed 21 May 2020, and 63/028,723, filed 22 May 2020, which are all incorporated by reference in its entirety.

BACKGROUND OF THE INVENTION

1. Field of Invention

This invention relates to a fluorometer for measuring the concentration of species-of-interest in a liquid; and more particularly, to a fluorometer for measuring the concentration of fluorophores in a liquid using non-intensity (i.e., amplitude) based measurements.

2. Description of Related Art

The phenomenon of optical fluorescence is commonly exploited for use in environmental water quality monitoring as such technology can be realized as a compact, field-rugged sensor. Fluorescence-based sensing consists of an excitation light source (at a specified optical wavelength), used to optically excite the water parameter of interest and re-emit light (at a longer optical wavelength) specific to the water parameter of interest.

Known fluorometers gauge the concentration of the water species by measuring the amplitude of the return fluorescence signal. The amplitude-based measurement is plagued with multiple issues:

1) Degradation of Excitation Source

Typical excitation sources include LEDs, laser diodes or lamps, all of which suffer from intensity degradation through the course of use. Options for dealing with source degradation are limited. One option is to include a reference detector, which will factor-out/nullify the effects of degradation, but adds complexity to the sensor's electrical circuit and requires additional opto-mechanical space. A second option is to periodically re-calibrate the sensor which necessarily limits the duration of field deployments.

2) Thermal Drift of Excitation Source

All of the sources mentioned above have a non-negligible response to temperature, i.e., the optical output power changes as the ambient temperature changes. This poses a real problem in sensor performance relying again on either a reference detector, or some elaborate electrical or embedded software compensation scheme. Furthermore, temperature compensation requires some measurement of the temperature sensor, usually enabled by an onboard (i.e., located internally within the electrical circuit) temperature sensor, requiring additional circuitry and physical space.

3) Interfering Species

Fluorescence-based sensors can suffer from optical interferences in which the presence of other competing species can absorb at the same respective target excitation and/or emission wavelengths, resulting in a decrease of fluorescence amplitude.

4) Opto-Mechanical Configuration

Traditional fluorescence sensing techniques suffer from poor sensitivity (especially field-deployable sensors) stemming from poor/inefficient capture of the fluorescence signal. Existing fluorescence sensors typically employ a single excitation light source and a single (point-like) emission receiver, utilizing a photosensitive element. Regardless of the particular photosensitive element or excitation light source used, known prior art is not opto-mechanically configured for efficient capture of fluorescence, resulting in compromised limit of detection.

5) Inner Filter Effect (IFE)—a Range Limiting Effect

Known prior art exhibits the following problem: At low concentrations, the fluorescence signal is approximately proportional to the species concentration. However, as the concentration is increased, the signal reaches a maximum followed by a decrease in the signal with ever higher concentrations. In this regard, traditional fluorometers are ambiguously double-valued, meaning that for any particular measured fluorescence signal, there are two possible concentrations—one high, one low. For these known fluorometers, there is no way to distinguish between the two possible outcomes.

Known Literature

There is known literature concerning fluorescence using 2-D arrays to estimate concentration gradients, and a brief summary of the major findings is presented below:

Known prior art discloses a 2-D array used for "the determination of concentration gradients in space and time". Here, the ("diffusion driven") concentration gradients are being determined by the local distribution and amplitude of fluorescence signal. This is an amplitude-based technique as the signal reported by any particular array element is simply proportional to the amount of "local" fluorescence (i.e., the local signal at a particular single array element), where the local amplitude of the fluorescence is understood to be proportional to the local fluorophore concentration density.

Moreover, see PCT/US2008/059575, filed 7 Apr. 2008, which discloses a system and method for high-throughput turbidity measurements, as well as an article by A Singh et al., entitled "The performance of 2D array detectors for light sheet based fluorescence correlation spectroscopy."

SUMMARY OF THE INVENTION

The present invention is distinctly different from the prior art described above:

For example, the present invention uses a spatial gradient (a consequence of Beer's law) to determine a single, fixed/quasi-static concentration, where changes in concentration in time are understood to change much slower than the required time for signal acquisition. Put another way, the spatial gradients for the sensor according to the present invention are a consequence of Beer's law and are not a result of some changing/varied spatial distribution of the fluorophore concentration.

In addition, the present invention circumvents many of the problems associated with amplitude-based fluorescence measurements while providing an opto-mechanical configuration, capable of greatly enhanced signal capture and elimination of IFE. The present invention employs a linear photodiode array (however, the present invention is not limited to photodiode technology, e.g., a linear CCD or CMOS array could also be used as well). A linear array allows a non-intensity-based determination of fluorescence. These measurements are spatially dependent, the main idea being that an optical signal will undergo attenuation across the linear array, following Beer's law, thereby creating a "spatial gradient". This spatial gradient contains information regarding the concentration of the fluorescent species.

The key element to the present invention deals specifically with the use of a linear sensor array to assess the spatial gradient of the signal along the length of the linear sensor array. The spatial gradient of the signal provides an assessment of the fluorophore concentration that offers many advantages over the known amplitude-based methods including:
Immunity to source degradation/drift,
Calibration-free sensing,
Immunity to florescence-band interference,
Enhanced signal sensitivity, and
IFE correction.

Other Implementation

The above "spatial gradient" method requires that each optical element in the array be individually addressable. However, there is a possible variant of the design that involves adding a transmission photodiode (located at the end of the array, opposite of the source) and connecting all of the linear array elements in an electrically parallel configuration. This design variant would further improve low signal sensitivity thereby further enhancing the minimum detection limit while retaining the sensor's ability to perform drift and IFE correction.

Finally, another variant could include the spatial gradient method in addition to the amplitude-based method to provide complementary information. Here the gradient-based method could be used to identify excitation degradation, while the amplitude based method could be used to bolster low signal detection.

Specific Embodiments

According to some embodiments, the present invention may include, or take the form of, apparatus featuring a signal processor or processing module configured to:
receive signaling containing information about light reflected off fluorophores in a liquid and sensed by a linear sensor array having a length and rows and columns of optical elements; and
determine corresponding signaling containing information about a fluorophore concentration of the liquid that depends on a spatial gradient of the light reflected and sensed along the length of the linear sensor array, based upon the signaling received The apparatus may include one or more of the following additional features:

The apparatus may include the linear sensor array.

The linear sensor array may include a linear photodiode array, a linear CCD array, or a linear CMOS array, as well as a closed cylinder sensor array having a three-dimensional cylindrical array of the rows and columns of the optical elements.

The spatial gradient may be determined by a linear array algorithm that defines a relationship between the fluorophore concentration [c], the length or location (l) along the linear sensor array, a species absorption coefficient ($\alpha$), and a signal (S(l)) of an array optical element along the linear sensor array.

The linear array algorithm takes the form of the equation:

$$y = mx + b,$$

where
$y = -\ln(S(l))$,
$mx = \alpha [c] l$, and
$b = -\ln([c]AT_0)$.

The linear array algorithm is based on Beer's law.

The apparatus may include, or take the form of, a spatial gradient-based fluorometer.

The apparatus may include a quasi-collimated light source having a corresponding length and being configured to provide the light, including quasi-collimated light, along the length of the linear sensor array.

The signal processor or processing module may be configured to determine the fluorophore concentration based upon an attenuation of an optical signal sensed across the linear sensor array, including along the length and/or width of the linear sensor array.

The linear sensor array may include a two-dimensional array of the optical elements that are individually addressable.

Either the rows or the columns of the optical elements may be connected in parallel and addressable by the signal processor or processing module; the apparatus may include a transmission photodiode located at an end of the linear sensor array, opposite the light source, configured to respond to the light reflected off the fluorophores and provide transmission photodiode signaling containing information about the same; and the signal processor or processing module may be configured to receive the photodiode signaling and correct the corresponding signaling for drift or the inner filter effect (IFE).

A Spatial Gradient-Based Fluorometer

By way of further example, and according to some embodiments, the present invention may include, or take the form of, a spatial gradient-based fluorometer featuring a quasi-collimated light source, a linear sensor array and a signal processor or processing module.

The quasi-collimated light source has a length and may be configured to provide quasi-collimated light to a liquid sample.

The linear sensor array has a corresponding length and rows and columns of optical elements and may be configured to sense light reflected off fluorophores in the liquid sample along the length of the collimated light source and provide signaling containing information about the light reflected off the fluorophores.

The signal processor or processing module may be configured to:
receive the signaling; and
determine corresponding signaling containing information about a fluorophore concentration of the liquid that depends on a spatial gradient of the light reflected and sensed along the corresponding length of the linear sensor array, based upon the signaling received The spatial gradient-based fluorometer may also include one or more of the features set forth above.

The Method

According to some embodiments, the present invention may include a method, featuring:
receiving, with a signal processor or processing module, signaling containing information about light reflected off fluorophores in a liquid and sensed by a linear sensor array having a length and rows and columns of optical elements; and
determining, with the signal processor or processing module, corresponding signaling containing information about a fluorophore concentration of the liquid that depends on a spatial gradient of the light reflected and sensed along the length of the linear sensor array, based upon the signaling received The method may also include one or more of the features set forth above.

Computer-Readable Storage Medium

According to some embodiments of the present invention, the present invention may also take the form of a computer-readable storage medium having computer-executable components for performing the steps of the aforementioned method. The computer-readable storage medium may also include one or more of the features set forth above.

Advantages

The present invention offers distinct advantages over the current known techniques in the prior art, as follows:

1) The present invention determines fluorophore concentrations through a spatial gradient (a fluorescence signal that changes across the length of the linear array detector in keeping with Beer's law) (See FIG. 1), and not by the amplitude of the fluorescence signal (algorithm for concentration determination (See FIG. 5)). As such, it is unaffected by moderate changes in the intensity of the source. This means that the spatial gradient is immune to source degradation, source thermal response, or change in source drive conditions (such as LED drive current). However, it is necessary that a non-negligible signal be present, i.e., there has to be some measurable amount of light incident upon the array to form the spatial gradient. Additionally, the elements need to be individually addressable to resolve the spatial information. The present invention is not limited to any specific linear array detector technology; a linear photodiode, CCD or CMOS array could be used.

2) The present invention, being immune to source degradation/drift, is capable of calibration-free deployments thereby extending the length of each deployment.

3) A linear sensor array provides a much larger overall active area to capture the return fluorescence. More importantly, the active area is larger in the dimension that matters most—along the optical axis (a quasi-collimated excitation source is often used which emits radiation predominantly along a single axis commonly referred to as the "optical" axis) (See FIG. 1). The increased capture of fluorescence greatly enhances the signal sensitivity which, in turn, leads to a significant improvement in the minimum limit of detection the fluorescence species.

4) Just as the gradient-based method is impervious to moderate changes in excitation power, it is also impervious to certain type of interferences. Any interfering species which absorbs the fluorescence signal, but not the excitation signal (fluorescence-band interference), will not affect the signal gradient and therefore not hinder any assessment of the fluorophore concentration. Note, the spatial gradient method cannot address any interfering species that does absorb the excitation signal (excitation-band interference) as this would affect the signature of the signal gradient.

5) While the fluorescence amplitude of traditional fluorometers suffers from an ambiguous double-valued response (due to IFE), such is not the case for the spatial gradient method whose response is monotonic with increasing concentration (See FIG. 4). The spatial gradient method enables real-time, inner filter effect (IFE) correction. [for the known prior art, the common method of inner filter correction involves post processing via lab analysis after a field deployment]. The IFE correction greatly enhances high-concentration sensing range (See FIG. 3).

BRIEF DESCRIPTION OF THE DRAWING

The drawing, which are not necessarily drawn to scale, includes FIGS. 1-8, as follows:

FIG. 5 is an algorithm to determine concentration from the spatial gradient, according to some embodiments of the present invention.

FIG. 6 is a block diagram of apparatus, including a spatial gradient-based fluorometer, according to some embodiments of the present invention.

FIG. 7 is a block diagram of a linear sensor array having a length and rows and columns of optical elements, according to some embodiments of the present invention.

Figure 1:
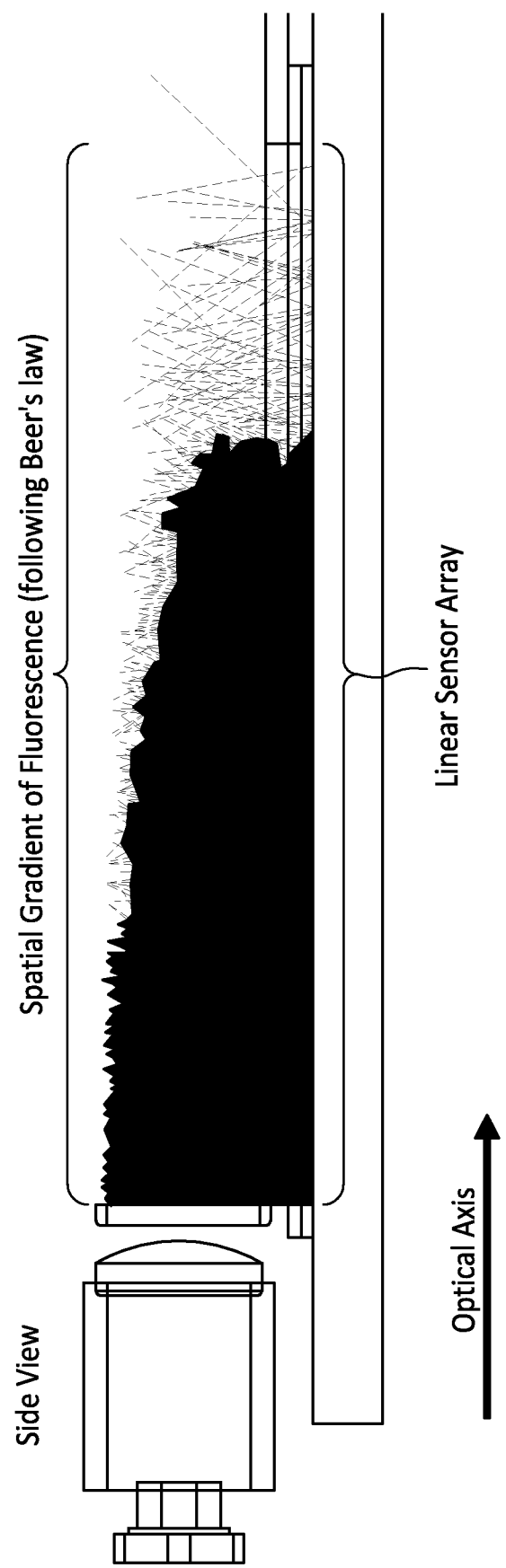
FIG. 1 is a side view of fluorescence "spatial gradient" following Beer's law (simulated in TracePro™).
Figures 2, 2A, 2B:
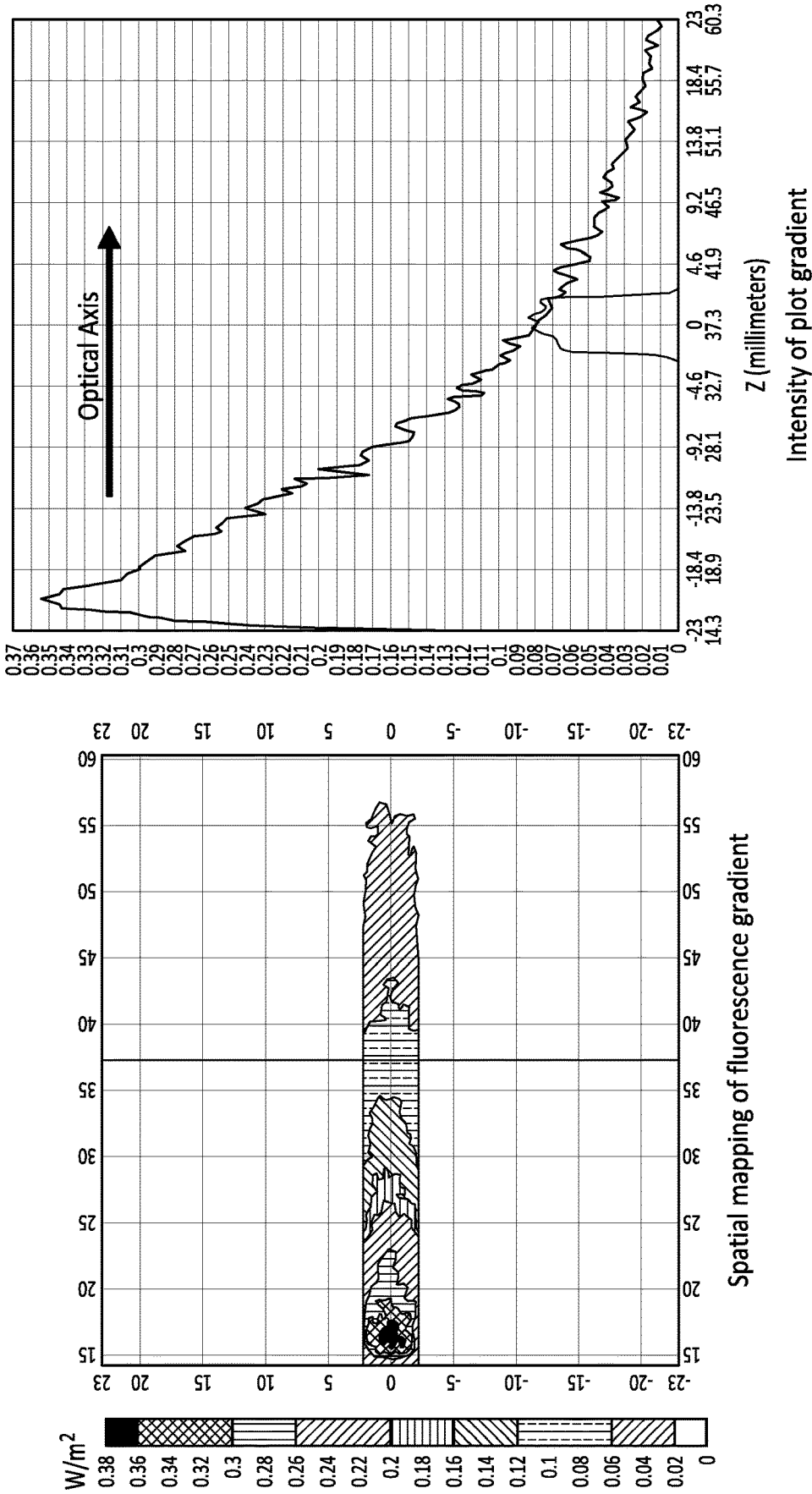
FIG. 2 includes FIGS. 2A and 2B that show a spatial mapping and intensity plot of fluorescence gradient (simulated in TracePro™).
Figure 3:
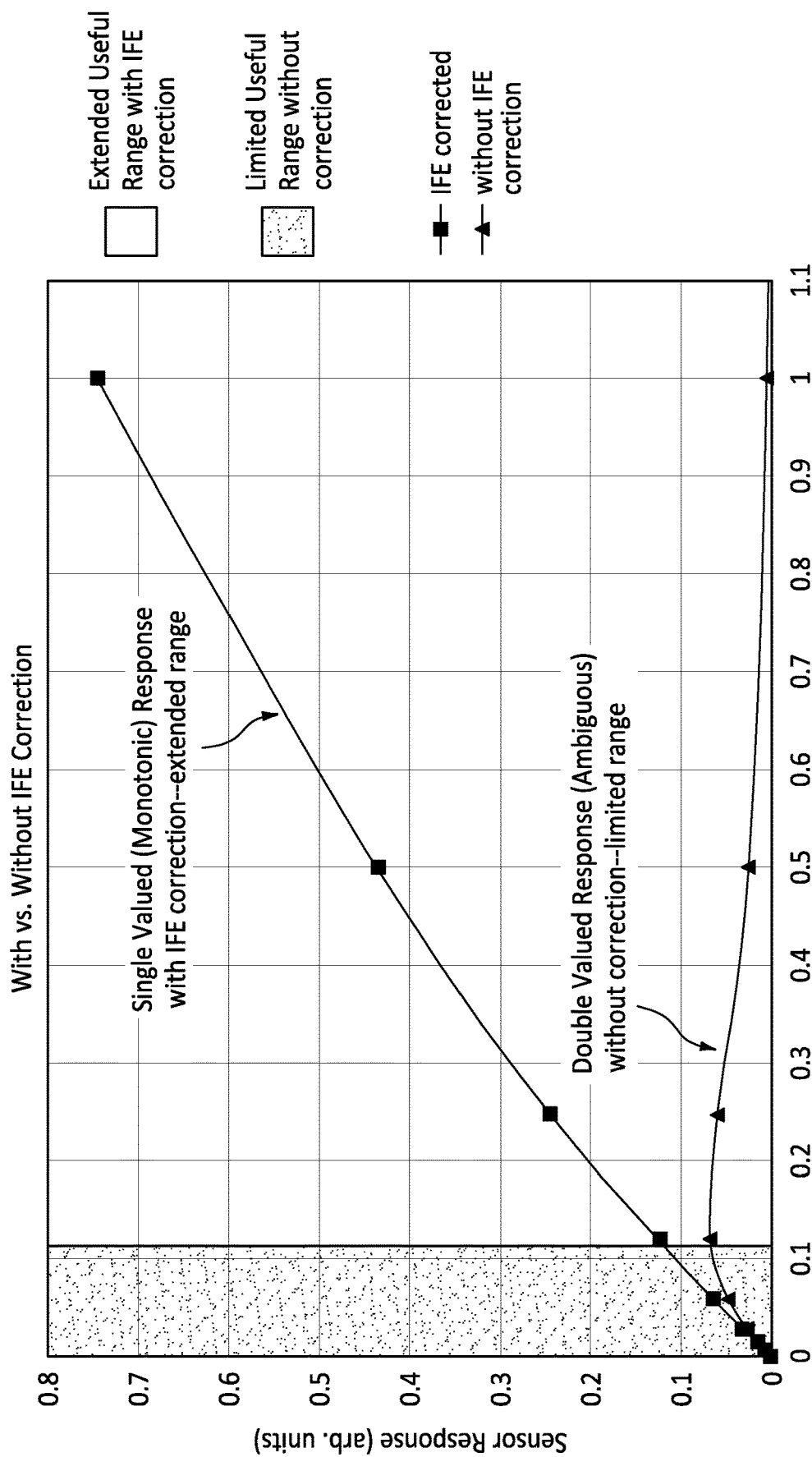
FIG. 3 is a graph of sensor response vs. relative concentration with and without IFE correction [illustrating 10X enhanced detection range] (simulated in TracePro™).
Figure 4:
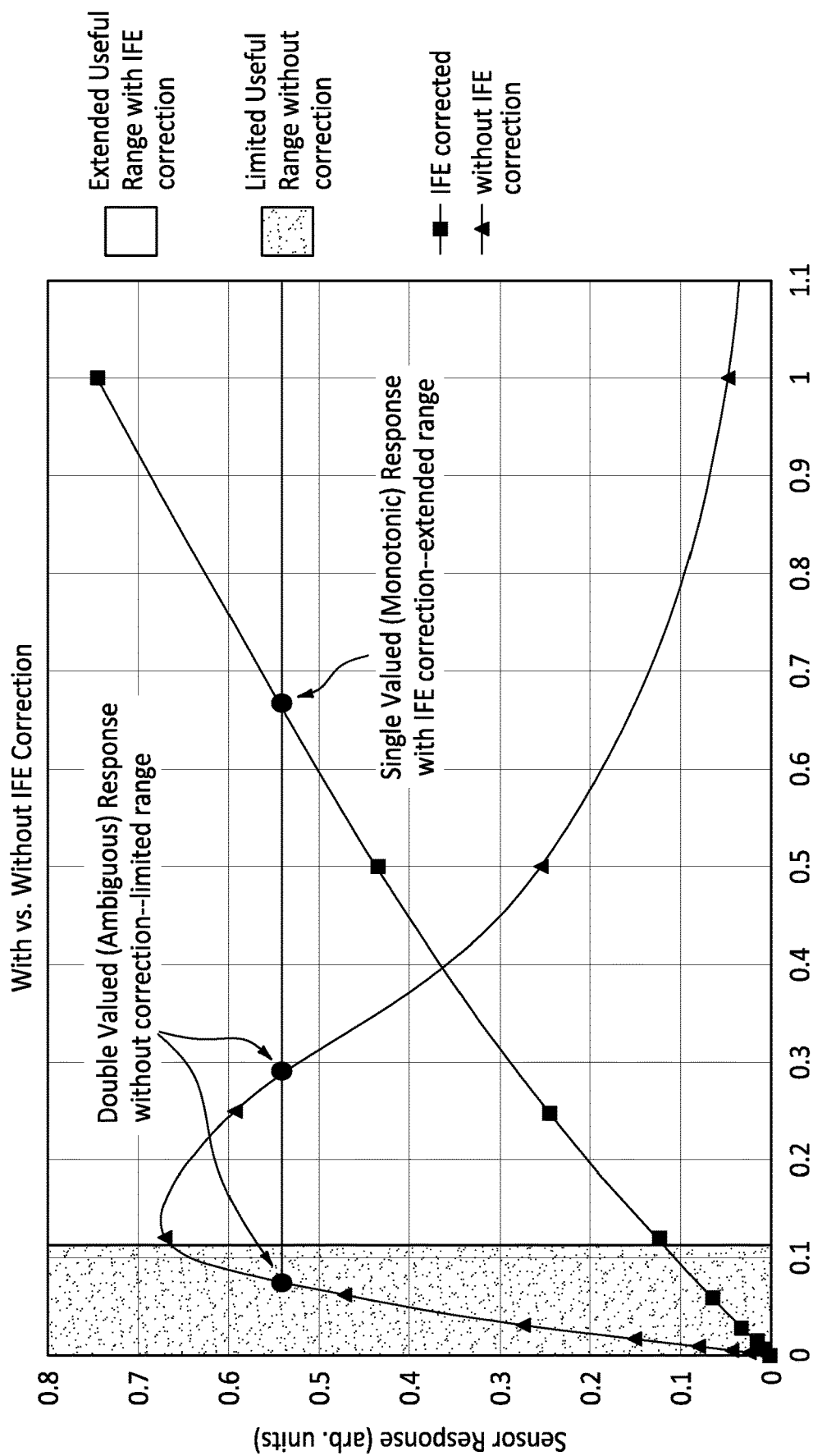
FIG. 4 is a graph of sensor response vs. relative concentration with and without IFE correction [elimination of double value problem] (simulated in TracePro™).

To reduce clutter in the drawing, each Figure in the drawing does not necessarily include every reference label for every element shown therein.

DETAILED DESCRIPTION OF BEST MODE OF THE INVENTION

FIG. 6 shows apparatus 10, including a spatial gradient-based fluorometer, according to the present invention having a quasi-collimated light source 20, a linear sensor array 30, and a signal processor or processing module 40.

Figure 8:
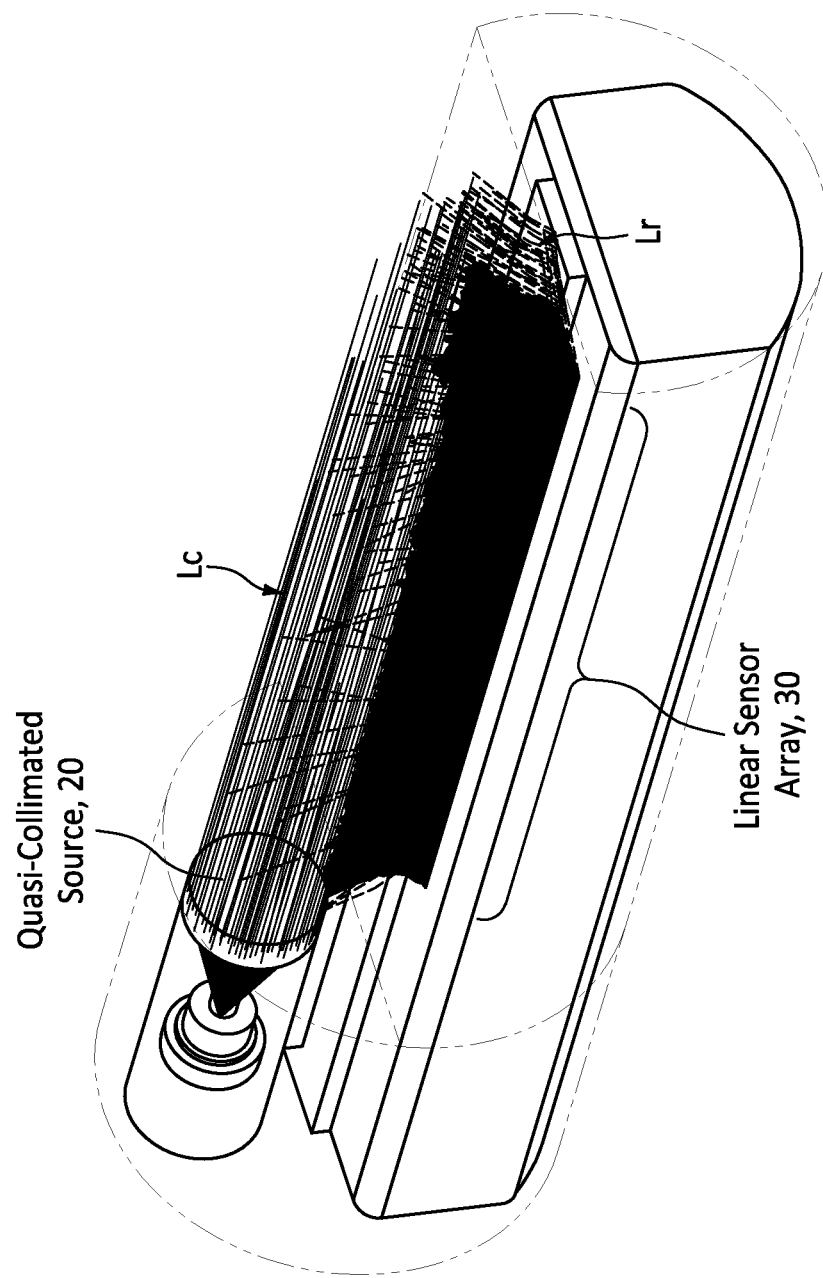
FIG. 8 is a three dimension perspective view of a quasi-collimated light source that provides a quasi-collimated light in relation to a linear sensor array, according to some embodiments of the present invention.

The signal processor or processing module 40 may be configured to receive signaling containing information about light Lr (FIG. 8) reflected off fluorophores in a liquid and sensed by the linear sensor array 30 having a length L and rows and columns of optical elements (r1, c1; r1, c2; r1, c3; r1, c4; r1, c5; r1, c6; r1, c7; r1, c8; . . . ; r1, cn; r2, c1; r2, c2; r2, c3; r2, c4; r2, c5; r2, c6; r2, c7; r2, c8; . . . ; r2, cn; r3, c1; r3, c2; r3, c3; r3, c4; r3, c5; r3, c6; r3, c7; r3, c8; . . . ; r3, cn; . . . ; rn, c1; rn, c2; rn, c3; rn, c4; rn, c5; rn, c6; rn, c7; rn, c8; . . . ; rn, cn), e.g., as shown in FIG. 7; and determine corresponding signaling containing information about a fluorophore concentration of the liquid that depends on a spatial gradient of the light reflected and sensed along the length L of the linear sensor array 30, based upon the signaling received

The Linear Sensor Array 30

By way of example, the apparatus 10 may include the linear sensor array 30, e.g., such as a linear photodiode array, a linear charge-coupled device (CCD) array, a linear CMOS array. By way of further example, the linear sensor array 30 may include a two-dimensional array of rows and columns of optical elements, e.g., like that shown in FIG. 7, that are individually addressable. Linear sensor arrays are known in the art, and the scope of the invention is not intended to be limited to any particular type or kind thereof either now known or later developed in the future.

By way of example, linear sensors arrays are disclosed in the following U.S. Pat. Nos. 9,020,202; 8,022,349; 7,956,341; 7,040,538; 5,252,818; and 4,193,057, which are all hereby incorporated by reference.

The Light Source 20

By way of example, the apparatus 10 may include the light source 20 configured to provide the light Lc (FIG. 8), including quasi-collimated light, along the length L of the linear sensor array 30 through a liquid sample arranged in relation to the light source 20 and the linear sensor array 30 so as to reflect the light Lr off the fluorophores in the liquid sample being monitored or tested onto the linear sensor array 30. See FIG. 8. For example, the light may be reflected radially and backwards, i.e., backscattered reflected light or radiation.

As a person skilled in the art would appreciate, quasi-collimated light sources are known in the art, and the scope of the invention is not intended to be limited to any particular type or kind thereof either now known or later developed in the future.

The Signal Processor or Processing Module 40

By way of example, the signal processor or processing module 40 may be configured to determine the fluorophore concentration based upon a spatial gradient of the optical signal sensed across the linear sensor array, e.g., consistent with that set forth in relation to FIG. 5.

In an alternative embodiment, either the rows or the columns of the optical elements may be connected in parallel and addressable by the signal processor or processing module 40; the apparatus 10 may include a transmission photodiode 30a located at an end of the linear sensor array 30, opposite the light source 20, configured to respond to the light reflected off the fluorophores and provide transmission photodiode signaling containing information about the same; and the signal processor or processing module 40 may be configured to receive the photodiode signaling and correct the corresponding signaling for drift or the inner filter effect.

Implementation of Signal Processing Functionality

By way of example, the functionality of the signal processor or processing module 40 may be implemented using hardware, software, firmware, or a combination thereof. In a typical software implementation, the signal processor 40 would include one or more microprocessor-based architectures having, e. g., at least one signal processor or microprocessor. One skilled in the art would be able to program with suitable program code such a microcontroller-based, or microprocessor-based, implementation to perform the signal processing functionality disclosed herein without undue experimentation.

The scope of the invention is not intended to be limited to any particular implementation using technology either now known or later developed in the future. The scope of the invention is intended to include implementing the functionality of the signal processor(s) as stand-alone processor, signal processor, or signal processor module, as well as separate processor or processor modules, as well as some combination thereof.

By way of example, the apparatus 10 may also include, e.g., other signal processor circuits or components generally indicated 50, including random access memory or memory module (RAM) and/or read only memory (ROM), input/output devices and control, and data and address buses connecting the same, and/or at least one input processor and at least one output processor, e.g., which would be appreciate by one skilled in the art.

By way of further example, the signal processor 40 may include, or take the form of, some combination of a signal processor and at least one memory including a computer program code, where the signal processor and at least one memory are configured to cause the system to implement the functionality of the present invention, e.g., to respond to signaling received and to determine the corresponding signaling, based upon the signaling received.

Inner Filter Effect (IFE)

As a person skilled in the art would appreciate, the IFE is a fluorescence spectroscopy phenomenon, e.g., where there is a decrease in fluorescence emission seen in concentrated solutions due to the absorption of exciting light by the fluorophore that is close to the incident beam and which significantly diminishes light that reaches the sample further away from it.

As a person skilled in the art would appreciate, techniques for correcting for the IFE are known in the art, and the scope of the invention is not intended to be limited to any particular type or kind thereof either now known or later developed in the future.

Beer's Law

As a person skilled in the art would appreciate, Beer's law is defined by the relationship, as follows:

$$A = \varepsilon b C,$$

where

A=absorbance, $\varepsilon$=molar absorptivity, b=length of the light path, and

C=concentration,

Fluorophores

As a person skilled in the art would appreciate, a fluorophore is a fluorescent chemical compound that can re-emit light upon excitation. Fluorophores typically contain several combined aromatic groups, or planar or cyclic molecules with $\pi$ bonds.

By way of example, fluorophores are sometimes used as a tracer in fluids, as a dye for staining of certain structures, as a substrate of enzymes, or as a probe or indicator (when fluorescence is affected by environmental aspects such as polarity or ions).

The scope of the invention is not intended to be limited to any particular type or kind of fluorophore either now known or later developed in the future.

Applications

The present invention has applications, e.g., in the basic parameter of water quality monitoring for freshwater applications, as well as drinking water monitoring.

The Scope of the Invention

While the invention has been described with reference to exemplary embodiments, it will be understood by those skilled in the art that various changes may be made, and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
    a signal processor or processing module configured to:
        receive signaling containing information about light reflected off fluorophores in a liquid and sensed by a linear sensor array having a length and rows and columns of optical elements; and
        determine corresponding signaling containing information about a fluorophore concentration of the liquid that depends on a spatial gradient of the light reflected and sensed along the length of the linear sensor array, based upon the signaling received.
2. Apparatus according to claim 1, wherein the signal processor or processing module is configured to determine the fluorophore concentration based upon an attenuation of an optical signal sensed across the length of the linear sensor array.
3. Apparatus according to claim 1, wherein the linear sensor array comprises a linear photodiode array, a linear CCD array or a linear CMOS array.
4. Apparatus according to claim 1, wherein the linear sensor array comprises a closed cylinder sensor array having a three-dimensional cylindrical array of the rows and columns of the optical elements.
5. Apparatus according to claim 1, wherein the spatial gradient is determined by a linear array algorithm that defines a relationship between the fluorophore concentration [c], the length or location (l) along the linear sensor array, a species absorption coefficient ($\alpha$), and a signal (S(l)) of an array optical element along the linear spatial array.
6. Apparatus according to claim 5, wherein the linear array algorithm takes the form of the equation:

$$y = mx + b,$$

where $y = -\ln(S(l))$,
$mx = \alpha[c]l$, and
$b = -\ln([c]AT_0)$.

7. Apparatus according to claim 6, wherein the linear array algorithm is based on Beer's law.
8. Apparatus according to claim 1, wherein the apparatus is a spatial gradient-based fluorometer.
9. Apparatus according to claim 1, wherein the apparatus comprises a quasi-collimated light source having a corresponding length and being configured to provide the light, including quasi-collimated light, along the length of the linear sensor array.
10. Apparatus according to claim 1, wherein the signal processor or processing module is configured to determine the fluorophore concentration based upon an attenuation of an optical signal sensed across the linear sensor array, including along the length and width of the linear sensor array.
11. Apparatus according to claim 1, wherein the linear sensor array comprises a two-dimensional array of the optical elements that are individually addressable.
12. Apparatus according to claim 1, wherein the optical elements are individually addressable by the signal processor or processing module.
13. Apparatus according to claim 12, wherein
    either the rows or the columns of the optical elements are connected in parallel and addressable by the signal processor or processing module;
    the apparatus includes a transmission photodiode located at an end of the linear sensor array, opposite the light source, configured to respond to the light reflected off the fluorophores and provide transmission photodiode signaling containing information about the same; and
    the signal processor or processing module is configured to receive the photodiode signaling and correct the corresponding signaling for drift or the inner filter effect.
14. A method comprising:
    receiving, with a signal processor or processing module, signaling containing information about light reflected off fluorophores in a liquid and sensed by a linear sensor array having a length and rows and columns of optical elements; and
    determining, with the signal processor or processing module, corresponding signaling containing information about a fluorophore concentration of the liquid that depends on a spatial gradient of the light reflected and sensed along the length of the linear sensor array, based upon the signaling received.
15. A method according to claim 14, wherein the method comprises configuring the linear sensor array as a linear photodiode array, a linear CCD array or a linear CMOS array.
16. A method according to claim 14, wherein the method comprises determining the fluorophore concentration based upon an attenuation of an optical signal sensed across the length of the linear sensor array.
17. A method according to claim 14, wherein the method comprises configuring a light source to provide the light, including using a quasi-collimated light source to provide quasi-collimated light.
18. A spatial gradient-based fluorometer comprising:
    a quasi-collimated light source having a length and being configured to provide quasi-collimated light to a liquid sample;
    a linear sensor array having a corresponding length and rows and columns of optical elements and configured to sense light reflected off fluorophores in the liquid sample along the length of the collimated light source and provide signaling containing information about the light reflected off the fluorophores; and
    a signal processor or processing module configured to:
        receive the signaling; and
        determine corresponding signaling containing information about a fluorophore concentration of the liquid that depends on a spatial gradient of the light reflected and sensed along the corresponding length of the linear sensor array, based upon the signaling received.

19. A spatial gradient-based fluorometer according to claim 18, wherein the linear sensor array comprises a linear photodiode array, a linear CCD array, or a linear CMOS array.

20. A spatial gradient-based fluorometer according to claim 18, wherein the spatial gradient is determined by a linear array algorithm that defines a relationship between the fluorophore concentration [c], the length or location (l) along the linear sensor array, a species absorption coefficient ($\alpha$), and a signal (S(l)) of an array optical element along the linear spatial array.

* * * * *